(12) United States Patent
Toumazou et al.

(10) Patent No.: US 11,312,930 B2
(45) Date of Patent: Apr. 26, 2022

(54) INTEGRATED NUCLEIC ACID TEXT SYSTEM, INSTRUMENT AND METHOD

(71) Applicant: DNAe Group Holdings Limited, London (GB)

(72) Inventors: Christofer Toumazou, London (GB); David Davidson, London (GB); Samuel Reed, London (GB)

(73) Assignee: DNAe Group Holdings Limited, London (GB)

( * ) Notice: Subject to any disclaimer, the term of this patent is extended or adjusted under 35 U.S.C. 154(b) by 23 days.

(21) Appl. No.: 15/306,554

(22) PCT Filed: Apr. 27, 2015

(86) PCT No.: PCT/EP2015/059097
§ 371 (c)(1),
(2) Date: Oct. 25, 2016

(87) PCT Pub. No.: WO2015/162301
PCT Pub. Date: Oct. 29, 2015

(65) Prior Publication Data
US 2017/0166848 A1 Jun. 15, 2017

(30) Foreign Application Priority Data
Apr. 25, 2014 (GB) ...................... 1407334

(51) Int. Cl.
*C12M 1/34* (2006.01)
*B01L 3/00* (2006.01)
(Continued)

(52) U.S. Cl.
CPC ............. *C12M 1/34* (2013.01); *B01L 3/5027* (2013.01); *C12M 41/48* (2013.01);
(Continued)

(58) Field of Classification Search
CPC . B01L 2300/0645; B01L 3/5027; C12M 1/34; C12M 41/48; C12Q 1/6825;
(Continued)

(56) References Cited

U.S. PATENT DOCUMENTS

| 6,235,471 B1 | 5/2001 | Knapp et al. |
| 2003/0064382 A1* | 4/2003 | Preparata ............. C12Q 1/6874 435/6.11 |
| 2010/0282617 A1* | 11/2010 | Rothberg ............. C12Q 1/6825 205/780.5 |

FOREIGN PATENT DOCUMENTS

| WO | 2004/083443 A1 | 9/2004 |
| WO | 2007106579 A2 | 9/2007 |

(Continued)

OTHER PUBLICATIONS

Dynamically | Definition of dynamically in English by Oxford Dictionaries, (n.d.). Retrieved from https://en.oxforddictionaries.com/definition/dynamically.*

(Continued)

*Primary Examiner* — Lydia Edwards
(74) *Attorney, Agent, or Firm* — Maier & Maier, PLLC

(57) ABSTRACT

A method of analysing nucleic acid using apparatus comprising a reaction chamber and plurality of sensors located in the base of the chamber, with each sensor preferably located within a respective well. The method comprises flowing a fluid containing the nucleic acid or fragments thereof into the reaction chamber. While the chamber is fully or at least partially sealed, amplification of the nucleic acid or said fragments is performed within the chamber using an amplification primer or primers whilst detecting the generation of amplicons using said sensors. Sequencing or hybridisation is then performed on the amplicons, and sequencing or hybridisation is detected using said sensors.

12 Claims, 9 Drawing Sheets

(51) Int. Cl.
    *B01L 99/00*     (2010.01)
    *C12Q 1/6825*    (2018.01)
    *C12Q 1/6844*    (2018.01)
    *C12M 1/36*      (2006.01)
    *C12Q 1/6874*    (2018.01)
    *G01N 27/414*    (2006.01)
    *B01L 7/00*      (2006.01)

(52) U.S. Cl.
    CPC ......... *C12Q 1/6825* (2013.01); *C12Q 1/6844* (2013.01); *C12Q 1/6874* (2013.01); *B01L 7/52* (2013.01); *B01L 2200/10* (2013.01); *B01L 2300/0645* (2013.01); *B01L 2300/087* (2013.01); *B01L 2300/0816* (2013.01); *G01N 27/4146* (2013.01)

(58) Field of Classification Search
    CPC ................ C12Q 1/6844; G06T 1/0028; G06T 2201/0051; G06T 2201/0202
    See application file for complete search history.

(56) References Cited

FOREIGN PATENT DOCUMENTS

| WO | 2012/058096 A1 | 5/2012 |
| WO | 2014013263 A1 | 1/2014 |

OTHER PUBLICATIONS

International Search Report and Opinion dated Dec. 15, 2015 in corresponding Application No. PCT/EP2015/059097; 17 pgs.
European Search Report dated Nov. 2, 2018, in connection with corresponding EP Application No. 15 720 669.9 (7 pgs.).

* cited by examiner

INTEGRATED NUCLEIC ACID TEXT SYSTEM, INSTRUMENT AND METHOD

TECHNICAL FIELD

The present invention relates to a system, instrument and method for processing nucleic acid. The invention facilitates control and operation of the workflow and components of the instrument/system. The processing may involve, by way of example, DNA/RNA sequencing and/or performing an immunoassay.

BACKGROUND

There have been significant breakthroughs in the development of biological assays. Such assays include immunoassays, DNA sequencing, analytical chemistry, and coulometry. Some of these assays have been developed as instruments for diagnostics. Many of these assays are quite complex and require specialised knowledge to operate and interpret.

Within the field of genetics there are applications for whole genome sequencing, de novo sequencing, gene expression analysis, and detecting single nucleotide polymorphisms (SNP). Each of these tests present different levels of information and complexity of testing. In certain cases more than one of these tests will be required and it is up to the clinician to decide how to progress.

Most test workflows have three major aspects: sample preparation, detection, and interpretation of the results. The sequencing by synthesis technique for genetics is an example of a complex process having many steps for each of these aspects.

The preparation phase may start with extraction of template nucleic acid from the sample provided, followed by purification, fragmentation of the nucleic acid into workable lengths, clonal amplification of the template fragments, hybridisation/ligation to a primer/probe, and ligation/immobilisation to a surface or bead. The sequencing by synthesis step itself requires flowing different nucleotide types (dNTPs) across the template colonies, wherein nucleotides become incorporated with the template nucleic acid.

The detection phase may employ various technologies such as electrophoresis, chemical luminescence and optical cameras, measuring electrode impedance/capacitance change, measuring immobilised DNA intrinsic charge change, or monitoring proton concentration with an Ion Sensitive Field Effect Transistor (ISFET).

The Interpretation phase is the analysis and extraction of information from the detection results. For example, this may include: determining the sequence of nucleotide incorporations detected from each fragment; determining their alignment/reassembly to form the whole genome; or their comparison with known sequences. The results may guide treatment or suggestion of complementary products, although the final result may be days after the initial sample collection.

Of the detection processes identified above, one of the most exciting involves the use of ISFETs and other chemical FETs (ChemFETs). The use of ISFETs to sequence DNA and DNA fragments (as well as RNA and RNA fragments) is described for example in WO03/073088. This work has demonstrated that the incorporation of nucleotides (A,T,C, G) during extension of a DNA strand can be monitored by using an ISFET to measure the variation in ionic concentration as a by-product of the reaction. When a nucleotide extends a DNA strand, it releases pyrophosphate which is hydrolysed and generates H+ ions, reducing the pH. In a similar way, an ISFET can be used to detect hybridisation whereby a hybridisation probe attaches to a matching sequence on a DNA strand.

An extension of this approach using very large scale FET arrays is described in US2009/0026082 and provides for massively parallel analysis. By analysing a large number of DNA fragments in parallel, and then aligning and "stitching" together the results, long sections of DNA may be sequenced in a relatively short time.

In the case of an ISFET based assay, the ISFET chip will be designed and manufactured to perform one or a set of predefined assays. For example, The ISFET chip will be configured to detect the presence of a set of SNPs in a sequence of DNA. The sample is first prepared on the laboratory bench. This may involve enriching the sample to remove material other than the cells, lysing the enriched cells to release the DNA, and performing amplification on one or more DNA sequences. During or following this process, the amplified DNA sequences are attached to micro beads. These beads are then introduced to the chip. This might involve depositing the beads into wells formed above the individual ISFETs, e.g. using magnetic beads to introduce one bead into each well. The chip can then be inserted into an instrument where the sequencing is performed. The instrument causes different nucleotides (A,T,C,G) to be flowed cyclically through the chip, with a washing step between each nucleotide flow. Electrical signals representing chain extensions are detected. The result provided by the instrument is a chain extension sequence for each ISFET. This data is then analysed, for example using a desktop PC connected to the analyser, to weigh the results according to their prevalence. Sequences that have a high prevalence will be recorded as valid sequences, whilst sequences with a relatively low prevalence will be recorded as being due to noise. The valid sequences may then be used to determine the presence or absence of a SNP(s) in the analysed sample. Of course other workflows and analysis routines are possible.

In addition to these essentially laboratory-bound assay processes, point-of-care assay procedures and systems have been developed. For example, DNA Electronics (London, UK) has developed a genetic testing kit that allows procedures such as that described above to be conducted by essentially unskilled persons at a point-of-care or point-of-sale. In many cases, testing using an ISFET-based assay will form only one part in a workflow that will be followed by a skilled technician. Based on the result of the ISFET-based assay, decisions may need to be made concerning further tests, and these tests will need to be performed, e.g. using further ISFET-based assays.

WO2011/034790 and US2012/0109531 present exemplary biological and physiological assay schemes and instruments that provide a degree of automation and flexibility. They are not however directly applicable to the handling of nucleic acids.

SUMMARY OF THE INVENTION

The inventors have envisaged a system able to flexibly run assays on a nucleic acid sample. Depending on the program that is run, different functions may be performed. These may be based on the data fed-back to optimise the instrument results.

In accordance with a first aspect of the present invention there is a method of analysing nucleic acid using apparatus comprising a reaction chamber and plurality of wells located in the base of the chamber, and at least one sensor located within each well. The method comprises flowing a fluid containing the nucleic acid or fragments thereof into the reaction chamber. While the chamber is fully or at least partially sealed, amplification of the nucleic acid or said fragments is performed within the chamber using an amplification primer or primers whilst the generation of amplicons may be detected using said sensors. Sequencing or hybridisation is then performed on the amplicons whilst detecting the sequencing or hybridisation using said sensors.

Other aspects of the invention are set out in the appended claims.

DESCRIPTION

A system and process are proposed, by way of example, that allow an integrated array of test elements (or "cells") to be configured to perform various assays and even reconfigured during the performance of an assay in dependence on intermediate results. In other words, intermediate decision points are introduced into the workflow followed by the assay, and the decisions made at each of the decision points determines how the workflow proceeds from that point, with the test elements being configured accordingly. Such configuring may involve controlling the flow of fluids into the test elements, for example to introduce appropriate primers and hybridisation probes and/or activate already deposited primers or hybridisation probes.

In a typical system, a chip comprises an integrated array of test elements, for example ISFETs, with different groups of test elements being arranged to perform different tasks. For example, a first group of ISFETs may be arranged to perform hybridisation to measure the similarity of a sequence of the DNA being analysed to a hybridisation probe bound within the test area. Further groups of ISFETs may be arranged to perform sequencing on respective different sections of the DNA under analysis. A decision point incorporated into the workflow makes a decision regarding which section of DNA to sequence based upon the result of the genotyping process.

Figure 1:
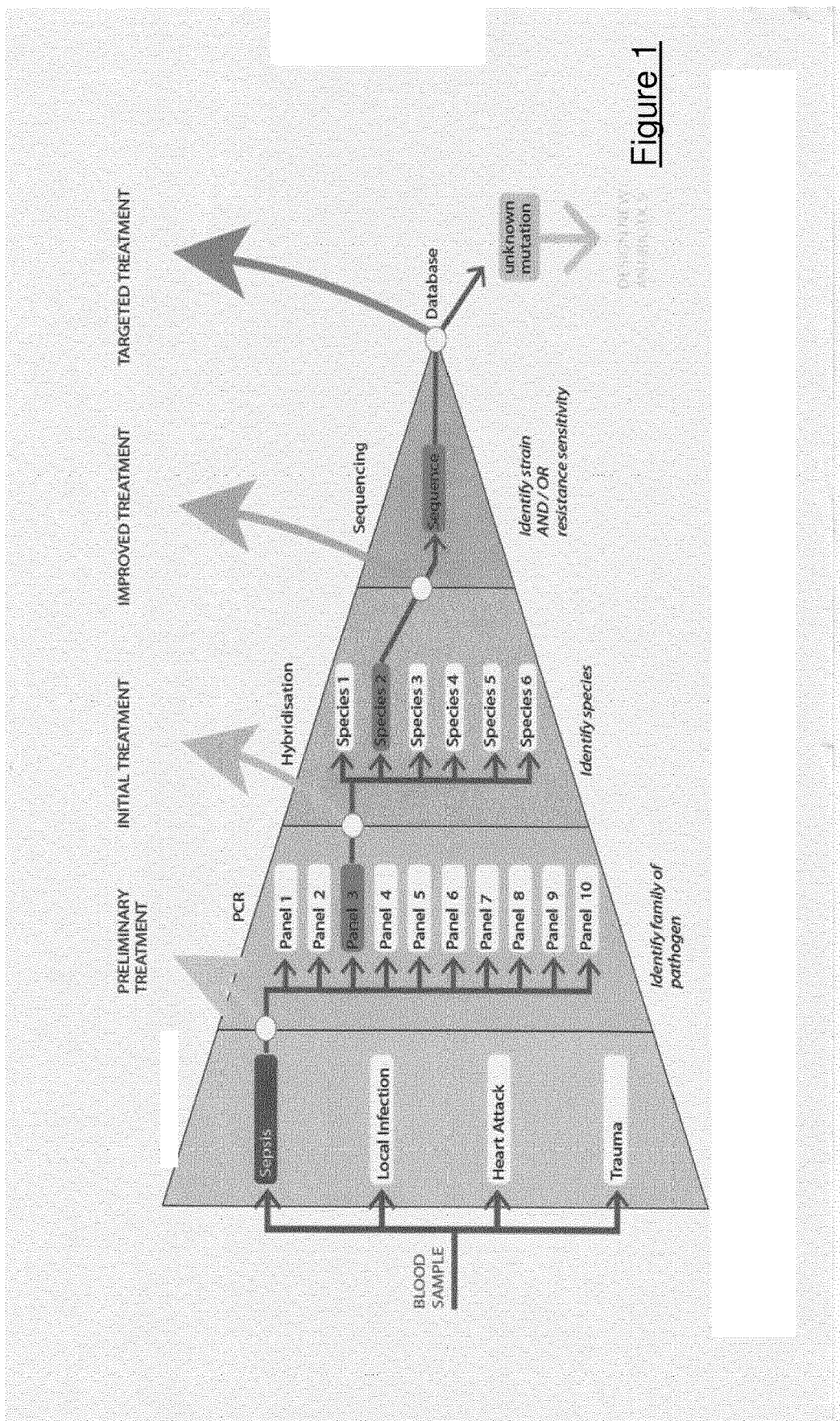
FIG. 1 illustrates an exemplary workflow carried out using a system comprising an array of test elements.

In an exemplary situation, a patient admitted to a hospital shows symptoms that could indicate trauma, heart attack, local infection or sepsis. The doctor must determine which of these is true and administer the appropriate treatment. Referring to FIG. 1, the horizontal axis represents an exemplary timeline for the resulting workflow on a particular sample. A blood sample is introduced to a sample ingress port of the test instrument incorporating an ISFET-based assay chip. The instrument may comprise pumps and valves, in conjunction with microfluidic flow channels and fluid gates, for directing the received sample to appropriate parts of the chip.

As a first phase of the workflow, diagnosis is made between conditions such as sepsis, local infection, trauma or Acute Myocardial Infarction (AMI). The result in this example is a diagnosis of sepsis.

It is now desirable to identify the family of the pathogen (to identify sepsis species and resistance genes) responsible for the infection. This is carried out by applying the extracted DNA to a set of ten PCR panels. These are selected as a result of the sepsis diagnosis. In some embodiments, all of the available modules are integrated onto a single chip whilst, in others, modules are provided on different chips. In any case, each of the ten PCR panels of the selected module is configured to perform PCR on a different targeted DNA sequence corresponding to a different family of pathogens. Each PCR Panel may comprise one or more wells each sitting above an ISFET sensor. An amplification primer may be immobilised at the base of each well or in solution, with different amplification primers for each Panel. The fluid control system is operated to cause a fluid containing all four nucleotides (A,T,C,G) to flow through each of the Panels. A heating and temperature sensing element is incorporated into the system to allow PCR amplification to be performed. In the example illustrated, a positive result is provided by Panel 3 (i.e. amplicons are generated—above some threshold level—only by Panel 3) thereby identifying the family of pathogens. In an alternative arrangement, rather than being immobilised within the wells, the amplification primers may be introduced into the panels via the fluid control system, e.g. together with the nucleotides.

In an alternative architecture, rather than having a plurality of modules available to perform different sets of PCR assays and selecting one of these based upon the triage diagnosis, a generic module may be provided with a set of panels that are "programmed" by flowing specific amplification primers through these, resulting in the immobilisation of the desired primers within the panels (or rather within the wells of the panels).

The third phase of the workflow is to identify the particular species of pathogen from within the identified family. In this embodiment this makes use of a set of hybridisation tests performed by six different modules, although this could alternatively be implemented by detection of amplification or sequencing, and the hybridisation phase may be omitted. Each module comprises one or more wells with each well sitting above an ISFET. A hybridisation probe is immobilised at the base of each well, with different probes for different modules. The sample, after preparation, is transported to the modules by appropriate operation of the fluid control system. A heating and temperature sensing element is incorporated into the system to allow hybridisation cycles to be performed repeatedly. In this example, a positive result is generated only by the Species 2 test. In an alternative arrangement, the hybridisation probes may be transported into the modules using the fluid control system.

As with the PCR modules, hybridisation modules may be selected from a greater number of available modules, or may be obtained by programming a set of generic modules so as to immobilise appropriate hybridisation primers in the appropriate wells, or may be pre-programmed.

Considering further the second (amplification/PCR) phase and the third (hybridisation) phase, as described, these may be performed by separate amplification and hybridisation modules. An alternative approach however is to perform these phases within the same modules. This might be achieved for example by performing and detecting amplification within a given module and then activating or utilizing hybridisation primers already immobilised within the module to allow hybridisation to be carried out and detected. The activation process may involve heating and removing a layer of wax within the wells of the module to expose underlying hybridisation primers, or the hybridisation may be activated by adjusting the temperature to facilitate hybridisation, or the hybridisation may occur during the amplification phase.

The fourth and final phase of the workflow is optionally to sequence the relevant section(s) of the DNA, again using an appropriate module of the chip. Sequencing first requires that the DNA segment(s) to be sequenced have been amplified. Amplification can be performed in a pre-chamber in fluid communication with the sequencing chambers, e.g. using PCR. Alternatively, amplification may be performed in the sequencing chambers themselves. Amplification proceeds as described above with respect to the second phase of the workflow. The sequencing chambers contain one or more wells, above respective ISFETs, with a sequencing primer being immobilised at the base of the wells. Again, the fluid control system is operated to cause the prepared blood sample to flow into the module. Nucleotides (A,T,C,G) are then flowed through the module in sequence. Sequencing of different segments of the DNA may be performed in parallel, with the result data being aligned and stitched together.

In some embodiments, sequencing may be performed within the same modules that are used to perform the phase 2 amplification and the phase 3 hybridisation.

The detected sequence(s) can then be added to a database and compared with known pathogens to determine if the pathogen is known or unknown. A recommendation for treatment may be given upon final completion, which could include use of a drug with a pharmaco-genetic relationship. An option may be available to perform genotyping tests for the tailored drug.

Identification of the sample at each phase leads to another assay having a plurality of further possible identities and so on. After each phase in the workflow, subsequent workflow decisions are made. Also the intermediate results can be used to inform treatment decisions. For example, if the result of the first phase indicates sepsis, preliminary treatment for that may begin. The second phase assay identifies what form of sepsis is present (viral, bacterial, fungal, etc). If the second phase identifies a bacterial presence, treatment with a broad spectrum antibiotic may be recommended. As the workflow progresses, further intermediate treatment decisions can be made.

Furthermore, it will be appreciated that, during a particular assay stage, decisions about the assay may be made. For example, during sequencing of a nucleic acid at the fourth phase, each base identification may be used to determine whether to continue sequencing for further identification, stop sequencing, or flow a particular order of nucleotides.

In the case of modules that perform amplification, by monitoring all reaction volumes it is possible to switch off or ignore any downstream processes for any chambers that show no amplification. For those chambers that do show amplification, a decision is needed on whether or not to proceed to the next stage of the process. For example, if a resistance gene is identified, this might provide enough information to make a recommendation to the physician to tailor the treatment specifically for this resistance gene and therefore the workflow for that sample might end at this stage. If, however, the resulting amplification is still ambiguous or requires further analysis, a decision can be made to progress to hybridisation and sequencing. Similarly to the amplification mode, monitoring these modes allows decisions to be made to progress or not, to continue to monitor downstream events or not, including stopping the test altogether and making a recommendation for treatment.

In the cases of either trauma or AMI being diagnosed, the opportunity exists to screen the patient for drug interaction information, for example establishing the genotype for drugs such as warfarin or PLAVIX. In both of these cases, the genotyping can be done on the sample collected during the triage (which will contain large amounts of the patient's cells and DNA). Genotyping can be determined using the first modality of the system—PCR or isothermal amplification and detection. There is not likely to be a need to progress beyond this stage.

Figure 2:
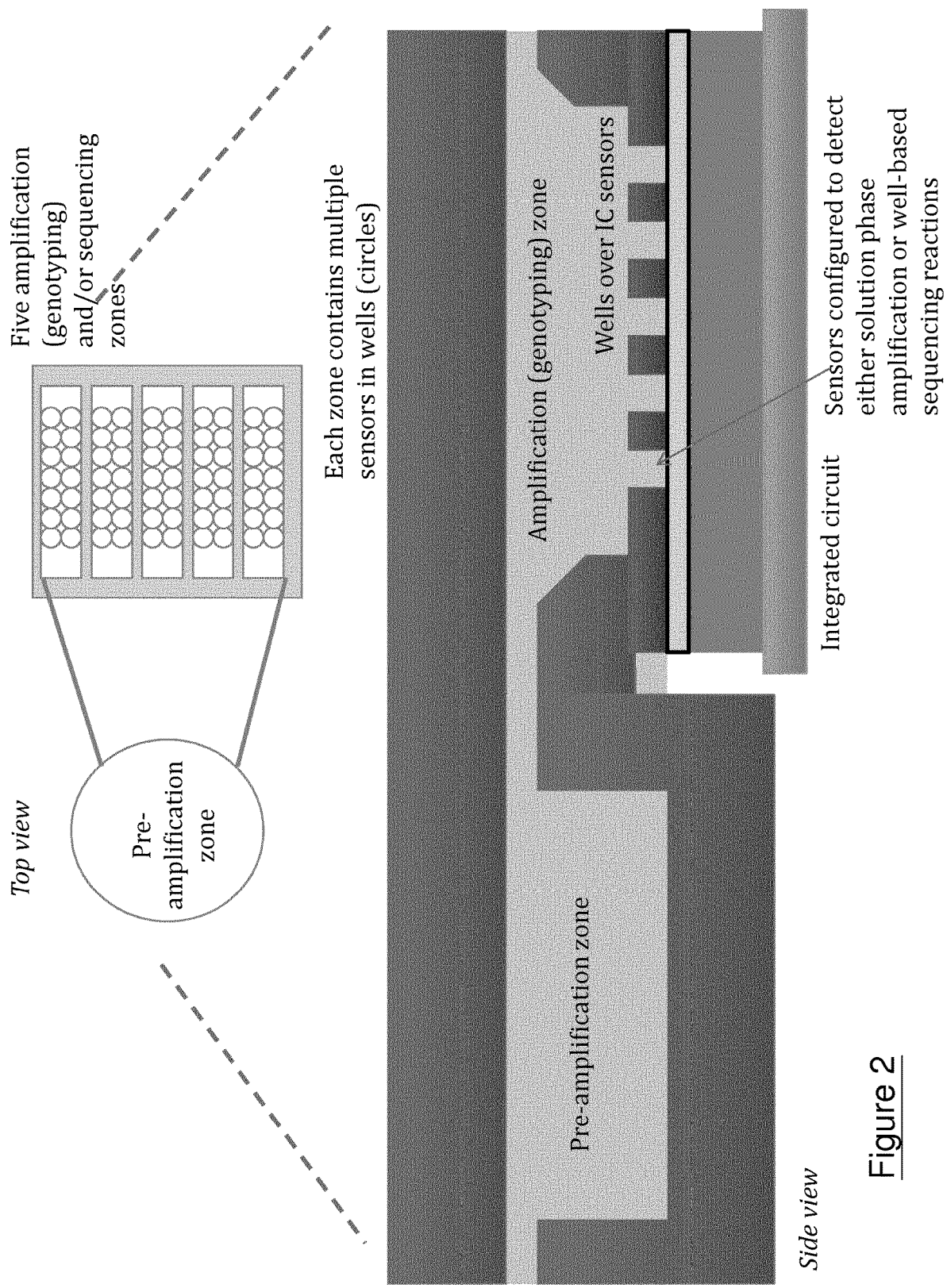
FIG. 2 illustrates a module of an ISFET-based chip suitable for use in implementing the workflow of FIG. 1.

FIG. 2 illustrates a module of an ISFET-based chip suitable for use in the process described above. This module, at least in terms of its physical structure, might be generic to all of the different assay types performed by an instrument (e.g. as exemplified by the above discussion with reference to FIG. 1), e.g. amplification, hybridisation and sequencing. In some cases the module may be configured to perform two or more of amplification, sequencing and hybridisation. To the left of the Figure there is illustrated a "pre-amp" stage that is configured to prepare a sample for subsequent genetic analysis. This stage may, for example, isolate cells in a blood sample and extract the DNA from the cells. The pre-amp stage then supplies the enriched sample to a reaction chamber comprising five wells, each exposed to ISFET sensors. The inset on the right hand side of the Figure illustrates a side, cross-sectional view through one of the row of sensors. Each of the reaction chambers comprises ingress and egress fluid ports, and a central space for holding a volume of fluid. The ISFET sensors are arranged on the base of the wells. Additionally, the module may comprise a heater and temperature sensor for heating fluid in the chambers.

Depending upon the assays to be performed, amplification and sequencing primers, and hybridisation probes, may be immobilised within the wells of the module. As a particular example, one might consider the case where the module is configured to perform amplification (PCR) followed by sequencing. In this case, the prepared sample, containing extracted and fragmented DNA, may be flowed into the chambers of the module together with an amplification primer and nucleotides. The temperature is then cycled to perform PCR amplification. Sequencing primers are immobilised within each well. Sequencing is then performed on the amplicons and the results read out from the ISFETs.

One approach to achieve multi-mode workflows is to have each mode assigned to a specific chip, and to assemble the chips into a cartridge such that the cartridge has all of the necessary modes but without having the ability or requirement to have each chip capable of switching between modes. This design would overcome anticipated challenges such as thermal compatibility and functionalization, but would bring with it a more complex design for the fluidic handling and control, etc.

In an alternative approach, a portfolio of test cartridges are available, each with specific functions or target diseases, and these can be selected dependent upon the results of earlier steps. Selection of the downstream tests (cartridges) could be an automated process or one involving a user-intervention (to plug two cartridges together, for example).

Some examples, all using the starting point of a triage system with sample enrichment, are as follows:

Trauma: On diagnosis of trauma, the appropriate downstream test may be to measure the pharmacogenomics profile of the patient for drug interaction information. The triage cartridge, used to make the diagnosis of trauma, effectively becomes the sample prep module and can be plugged/slotted into the appropriate trauma cartridge for the subsequent genotyping reactions to be executed.

Sepsis: the appropriate downstream test may be to identify the specific species or strain, and also identify any resistance genes that exist in the individual. The enriched sample from the triage component can be plugged into the sepsis cartridge and downstream analysis follows. There is the possibility that the prescribed treatment has a genetic factor to consider, and there is the option to genotype the individual. Again, either the triage sample could be used to run genotyping tests (or these could be standalone rapid tests).

Local infection: the appropriate test would be determined using other information provided, including physician observations, to select the appropriate panel of tests. Because the site of infection and/or the cause of the insult will influence the tests to be performed, it is reasonable to picture a number of different cartridges being available (as opposed to having one cartridge to cover all potential infections within a hospital environment). To make the system optimal, there could be a need to plug in the relevant test cartridge, which will be influenced by several factors and data.

Figure 3:
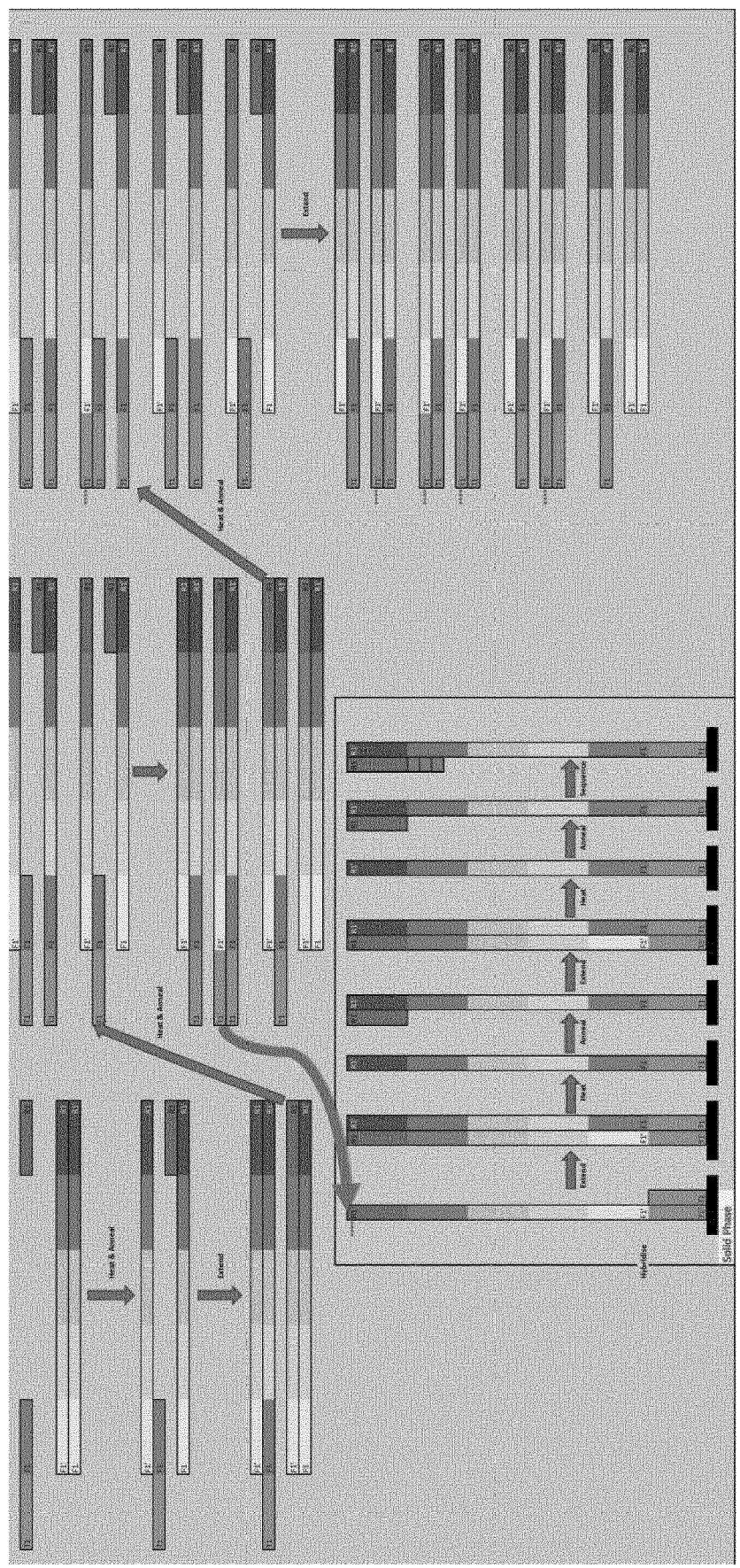
FIG. 3 illustrates schematically various biological operations that may form part of the workflow of FIG. 1.

Considering now FIG. 3, this illustrates an example process for analysing a sample of DNA. It is assumed that functionality has been assigned to a chip by depositing specific primers to known regions/wells within the chip. Given that it is known a priori what has been deposited and where, it can be determined what has been amplified based upon the sequences used for the primers. In this example, the primers used in the initial mode of amplification get modified with the corresponding sequence from the sample and ultimately are used to generate the product to be sequenced later in the workflow.

A sample enters the reaction chamber, amplification takes place (with real time detection) and the printed primers are modified to reflect the target sequence. After the amplification mode has completed, solution-phase primers are flushed away and replaced by sequencing primers. Being able to detect the hybridisation event might provide additional sequence information. Sequencing can then follow by flowing one or more nucleotides across the reaction chamber.

This system will require a less sophisticated fluid handling and control system compared to other methods, but may require additional mechanical actuations to allow different modes to follow each other.

In principle, the system has the ability to perform the amplification mode, detect any amplification that takes place, and can decide whether or not to proceed to the next stage. In instances where there is no amplification, the system can determine not to monitor any downstream reactions, or to stop any further reactions taking place. Similarly for the subsequent modes, failure to detect hybridisation can switch off the downstream sequencing mode whereas detection of hybridisation can allow a decision to be made to progress or not.

An instrument comprising or for use with the chips/modules described above comprises an operating system for interfacing with the components of the instrument and is arranged to receive data to configure or reconfigure the instrument. In certain embodiments, the instrument is arranged to receive real time data representing biological data about the sample, and the operating system can reconfigure the workflow of a test on the sample or reprogram components of the instrument. In this sense there is feedback of the test data to the instrument to operate the instrument in an optimal way. In certain embodiments, the instrument is arranged to receive data from an external source or an application running on the operating system and the operating system can configure the instrument to run biological tests in a customised way.

Figure 4:
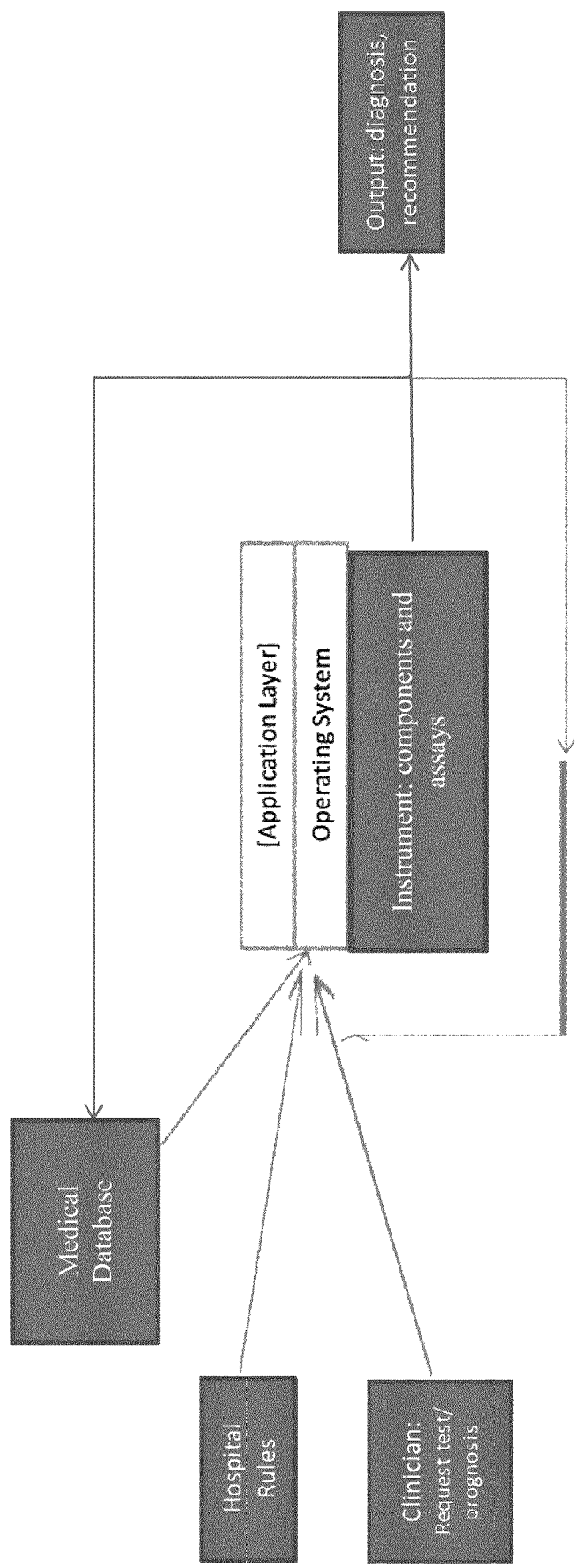
FIG. 4 illustrates schematically an instrument for implementing a workflow such as that illustrated in FIG. 1.

FIG. 4 illustrates at a very high level an instrument including a chip as described above, including both an operating system and an application layer (comprising one or more applications). The instrument receives input, which may be automated or manual input, from a variety of sources. The Figure suggests three sources: An application medical database, hospital rules, and clinician generated input. The instrument provides as an output a diagnosis and/or a recommended treatment regime.

Figure 5:
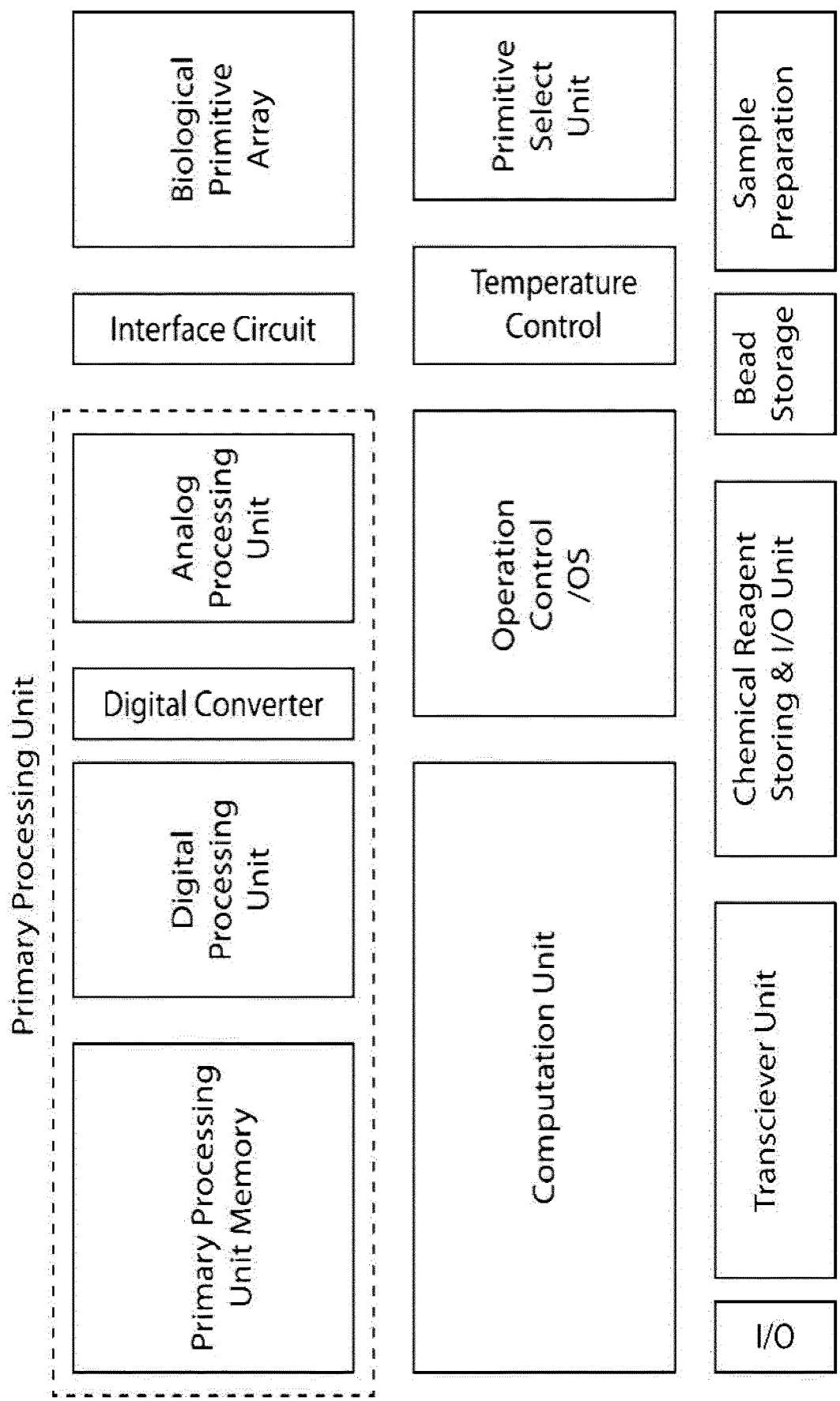
FIG. 5 is a block diagram of conceptual elements of the instrument of FIG. 4.

The physical components of a biological instrument will depend on the assay type and technology employed. FIG. 5 is a block diagram of conceptual elements of an instrument according to a preferred embodiment.

A sample preparation device;
A cartridge comprises the means to combine the sample and reagents for a bio-chemical reaction to create complexes to be detected;
A microfluidic network ensures that the sample and reagents are directed from component to component in a controlled way;
Reagents are stored within the instrument connected to piping and pumps, where valves and solenoids control the flow of the reagents;
A sensor or sensor array proximate or integrated with the cartridge detects signals from or properties of the complex.
An interface circuit is coupled to the sensor(s) to read out the electrical signals from the sensors
A control board comprises
A signal processors
ACPU/controller
A memory
An OS
An application layer While certain embodiments of the OS may be used with a moderately complex assay such as an ELISA, preferred embodiments are used with complex instruments with longer, flexible workflows and which provide greater depth of data. Complex instruments and assays, such as genetic sequencers, provide a large data stream which can be fed back to the OS and offer a number of decision points to change the workflow or select different assays.

In an exemplary instrument:
the assay is DNA sequencing;
the sensor cartridge is a semiconductor chip having a massive array of ISFETs;
the sample preparation comprises emulsion PCR on the template and binding to separate beads provided to wells proximate the ISFETs;
the reagents dATP, dTTP, dCTP, dGTP and wash are provided by a pump to the wells;
the ISFET signal is read one row at a time to a multiplexed array of analogue to digital converters (ADC);

the signal processor filters and determines nucleotide incorporation events, which are stored in a massive memory.

The Operating System controls these components and workflow.

Preferred embodiments of the instrument may be designed to accept a particular biological sample from a patient such as: blood, saliva, stool, mucus, etc.

The Operating System provides an interface between the instrument hardware and an application layer which contains a set of instructions to run the instrument. The OS may be considered similar to a combination of the BIOS (Basic Input Output System) and the conventional Operating System of a personal computer. The OS has access to and control of the components of the instrument such that it can turn them on/off or set properties of them. The OS defines how instructions affect the instrument and is responsible for translating the high level instructions into low level control of the components. The OS may also be designed to safeguard the instrument, for example by ensuring that the order of instructions is logical or parameters requested are within design limits.

Figure 6:
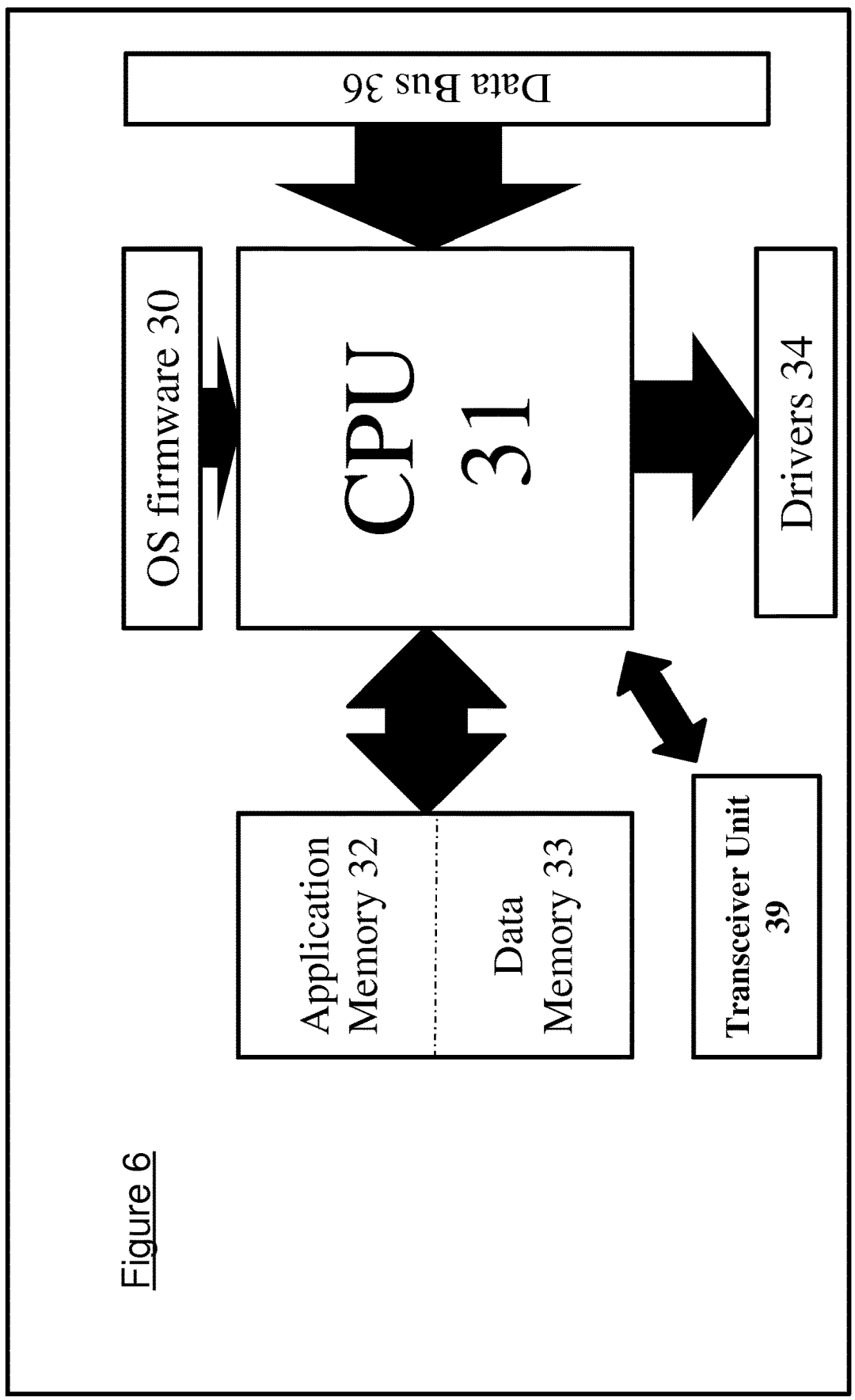
FIG. 6 illustrates schematically hardware and software components for implementing an Operating System.

The OS comprises hardware and software aspects. The hardware may comprise a control board having a processor, a memory, a data bus, and component drivers. The control board may be electrically connected to further hardware elements of the instrument such as a sensing chip, or it may share the board with such further hardware elements. The software aspect is encoded into non-volatile memory, preferably on the control board, and determines the operation of the OS hardware. Whilst various OS systems may be designed using well known architecture for receiving and processing signals and instructions to control instrumentation, an exemplary embodiment is illustrated in FIG. 6 and described below.

A non-volatile memory programmed with the OS code forms the OS firmware 30. When this code is read by the CPU 31, the control board is able to operate the instrument. One or more applications may be stored on a memory 32 to provide machine instructions for controlling the instrument in a customised way. The CPU reads code from the application memory 32 which is interpreted by the OS to create instructions for controlling the instrument. The CPU receives data from external sources on data bus 36. The data may be sensor data about the biological sample, data about the instrument hardware, and control feedback data. The data may be digital data or analogue data in which case the control chip will also comprise analogue to digital converters. The data may be stored into a data memory 33. The processor 38 is coupled to a plurality of drivers 34 which provide signals to operate components. For example, the drivers may open or close a reagent valve (digital control) or control the temperature of a heater (analogue or PWM control). The control board may also comprise a transceiver and data port for communicating with external devices.

In computer science terms, the OS may include Dynamically Linked Libraries (DLLs) which provide code blocks which may be called from applications. They are a shared and reusable resource. The advantage of DLLs are the provision of commonly used code, saving reprogramming by each application and ensuring that certain functionalities are robust. For example, in a genetic instrument, a DLL may implement PCR of a sample on a cartridge. In pseudo-code the application might simply instruct:

PCR (number_cycles)

Which the OS implements with a set of code that turn on heaters to set the temperature of the cartridge to a denaturing temperature, hybridisation temperature, and extension temperature with suitable delays between steps and repeats this cycle based on the parameter 'number_cycles'. The application is saved from re-writing this code and the temperatures will not exceed design limits.

Equivalent to the control board of FIG. 6, a single large integrated semiconductor chip may be fabricated incorporating memory, processor, drivers and data input/output connections.

Alternatively, the instrument may have a data port coupled to the instrument components and arranged to receive control signals and send data through the data port to a remote computer. The remote computer would comprise a processor and OS and be arranged to receive data from the instrument, run applications, and send controls signals to the instrument. In this scenario, the instrument system would comprise the instrument components and the remote computer.

Conceptually the instructions may be provided to the OS by a separate application layer or held in a memory part of the control chip. The invention is not intended to be limited by the architecture which provides the instructions to the OS.

The approach presented here considers different levels at which the system may be configured and/or reconfigured between the action of a user requesting a test and the generation of test results. Depending on the test requested and the data received, the operating system may make changes to the workflow or operation of hardware components. The instrument is thus able to optimise each test and it is conceivable that no two tests will be run the same.

If a single instrument is termed a system, then a group of instruments or instrument and peripheral hardware may be called a super-system. Components of the instrument may be called sub-systems. Examples of peripheral hardware include sample preparation devices, bioinformatics computers, etc. Examples of instrument components include reagent delivery units, sensors, cartridges, etc.

At the super-system level, a combination of instruments and/or peripheral devices are connectable such that the sample may be arranged to flow to a plurality of the instruments or peripheral devices for processing. For example, the OS may receive data about the sample type (blood, saliva, etc) and choose a particular sample preparation device and run conditions. In another example, the OS may decide to test a sample on multiple instruments in parallel to obtain a faster, more complete result.

At the system level, the OS may enter a mode of testing or a select a particular type of test cartridge, (selecting a sepsis/onco chip, with routes for phase I or phase II testing).

At the sub-system level, circuits on the chip may be configured to switch sensors, heaters, noise filters, and data acquisition elements on or off.

Further examples of re-configurability are provided below.

At the Super-System Level, the OS receives past test data and determines that there is an endemic Hospital Acquired Infection and arranges for all instruments to perform screening on all samples using infectious disease assays. The OS would select these assays in addition to the assay selected by the user. The OS might change the workflow, normally requiring determination of the infection variant for subsequent tests, by assuming that all patients have the same local disease and stopping deep DNA sequencing once the OS has confirmed the presence of the infection. The OS could then communicate with an external device to report the endemic infection to the hospital or government health agencies.

At the Sensor Chip level, data processing could be improved by modifying or selecting different circuit parameters based on initial sensor signal quality that suggest high background noise. The OS could redirect the raw sensor signal through a filter that rejects certain noise to allow real time signal improvement rather than need to discard the whole data set at a later date.

At a GSIC level, the OS could direct one or more GSICs to amplify DNA in their reaction well. Each GSIC would set the heater temperature, reference electrode voltage, sensor voltage and accept reagents as needed to comply. If the OS receives sensor data indicating poor copy count in a particular well, it could reinstruct the respective GSIC to further amplify the DNA in that well.

The OS control of the instrument components may be at a simple or complex level. For example at a high level the OS could simply instruct a component to perform a function or achieve a setting, wherein local circuitry would ensure compliance. At a complex level the OS could constantly monitor and control a component to achieve a function or setting.

To provide reconfiguration of the instrument components or workflow during testing, the OS is arranged to receive real-time data from the instrument. The data may be sensor data about the biological sample. The data is real-time in the sense of being generated by sensors during the test run, and not limited to data that is produced at a given instant in time.

The CPU may have dedicated ports to capture events or important signals. This enables the OS to be event driven, making decisions about reconfiguring the instrument as and when events occur. Alternatively the CPU may fetch data from memory 33 at points determined by the OS or application, such as when a decision point is reached in the workflow. The latter is appropriate where there is a large stream of data and the OS determines the best time to make decisions. For example, with a genetic assay, the OS may wait until an event is received indicating that gene-specific amplification has finished before deciding whether to do sequencing. The OS may then periodically recall data from memory about the sequences of particular wells to decide when to stop sequencing.

An application layer may be provided to interface with the OS layer. One or more applications may be loaded onto a memory to provide machine instructions to the OS to operate the instrument in a specific way. An application is a set of machine instructions readable by an Operating System. The application may be preinstalled with the instrument or loaded by a user. The program may be customised for a particular user (such as a hospital) to run a specific genetic test (such as detect infectious disease from a blood sample) according to a specific workflow (such as repetition of one process or skipping of another process).

In preferred embodiments, the application is responsible for configuring or reconfiguring the instrument hardware and workflow. For example, an application installed by a particular hospital might instruct deeper sequencing of a sample if it detects that a certain virus has been detected. The hospital might have a policy to check all samples for this particular viral strain that is now endemic to a ward such that future tests become reconfigured in addition to what the user requested.

The application may provide the interface for the user to the instrument. Different applications may provide different options to their users, from a single start button to a complex array of options providing flexibility. The OS interprets the applications' instructions but maintains overall control and responsibility of the instrument. For example the program may instruct the flowing of a reagent but the OS has more direct control of the pumps and valves and may override a request to pump a reagent once it has been consumed.

In a further embodiment, the application is loaded onto and operable from a computer external to the instrument. This remote computer may be a server, tablet, cloud computer, or smartphone, and maybe connectable to other computers. The instrument is connectable to this remote computer, preferably via a port on the control board. This connection allows the remote computer to receive biological test data from the instrument and send instructions to the OS. The remote computer may contain or be able to access a database of medical data about the patient providing the sample. This remote application may implement case-base-reasoning, heuristics for medical decision making, or machine learning such that the application can use the medical data to make intelligent decisions about how to configure the instrument. This may include instructing the instrument OS to use a particular workflow, set component settings, and/or run a particular assay. The remote application may receive real time data from the OS to revise its decisions and reconfigure the instrument.

For example, a doctor using the remote application requests testing for a patient. The remote application recalls the patient's medical history and physiological results and compares these to similar medical cases to recommend a genetic test to detect the presence of known cancer biomarkers. The application instructs the OS to load an oncology assay cartridge. The application can optimise the sequencing workflow knowing which bases are predominant for these genes. Having received real-time data from the instrument about certain genes, the application instructs the instrument to stop further sequencing. The application then instructs the instrument to load an assay to test for the patient's response to certain treatments. The application receives the final genetic results, adds them to the medical database, and outputs a therapeutic recommendation to the doctor. The application continues to build correlations between the genetic results and the medical database to update its case-based-reasoning, such that future similar cases may be tested in a more refined way on the instrument.

To enable the instrument to be particularly flexible and customisable, the instrument is arranged to accept and install one or more applications into a memory. These applications may be written by third parties desiring to optimise the instrument operation or implement particular protocols. This allows for third parties to experiment with and optimise the instrument's workflow and components. Alternatively certain users may have specific needs, provide a certain preferred sample type, or need to implement specific medical protocols or medical insurance policies. The application provides instructions to configure the instrument before testing starts and/or reconfigure the instrument upon receiving real-time data from the OS.

For example, a particular hospital only uses blood samples and desires to test each sample for a E. coli in addition to any test requested, and achieve a 90% confidence interval for certain biomarkers. The application instructs the instrument to purify the sample in a particular way optimised to capture patient and microbial components and then run both a bacteria assay cartridge and human genotype cartridge. Only a simple presence/absence test is requested for the bacteria cartridge whereas deeper sequencing is requested for the human genotype cartridge. The OS receives and sends real-time data to the application, which requests the OS to further sequence the DNA to determine antibiotics resistance if particular bacteria is present and the patient data indicates adversity to antibiotics, or to rerun a test if either result is identified by the OS as less than 90% reliable.

The OS is designed to receive "machine code" and translate these into output signals to control the assay. Machine code is usually a binary string compiled from code written in a high level programming language such as C++. Depending on the implementation of the OS, the machine code might provide simplified, high level instructions or more customisable low level instructions. As an example, the instructions in pseudo-code might include the following.

High level instructions:
Run sample prep
Purify sample
Lysis operation
Run oncology screen test
Run sepsis test
Run lifestyle test
Send data to insurer
Read patient profile
Run sequencing test
Read gene type
Output genotype to cloud
Reassemble sequence
Medical_association (genotype)
Drug_association (genotype)
QuantifyDNA
Low level instructions:
Flow nucleotide (A, T, C, G)
Run PCR (temp1, period1, temp2, period2, temp1, period3, cycles)
Wash assay
Load bead (z) into well (x, y)
Read results for GSIC (x, y)
Synthesize primer (ATCCGGTTA)
Heat wells (54 deg C.)
Filter_data (filter type, parameters)
ADC (parameters)

The application may include or have access to a database of biological values such as genotypes, antibodies, SNPs, microbial species that can be compared to the biological data output from an assay. Each data entry in the database may have one or more associated diagnostic, medical, or drug parameters. Each data entry in the database may be associated with a set of instructions. The application receives data from the assay and compares this to the database to determine the species or variant, find a recommended drug or therapy, or run the set of instructions. This expedites the procedure from receiving data and providing a meaningful output. For example, in a DNA sequencing assay where the data output is a stream of bases on the template nucleic acid, the application looks up each base or partial sequence of bases in the database. Some of these will return no useful association for which the application does nothing. Some of these bases will identify the species of the microbe in the sample and the database may contain instructions to continue sequencing to determine the particular variant.

Figure 7:
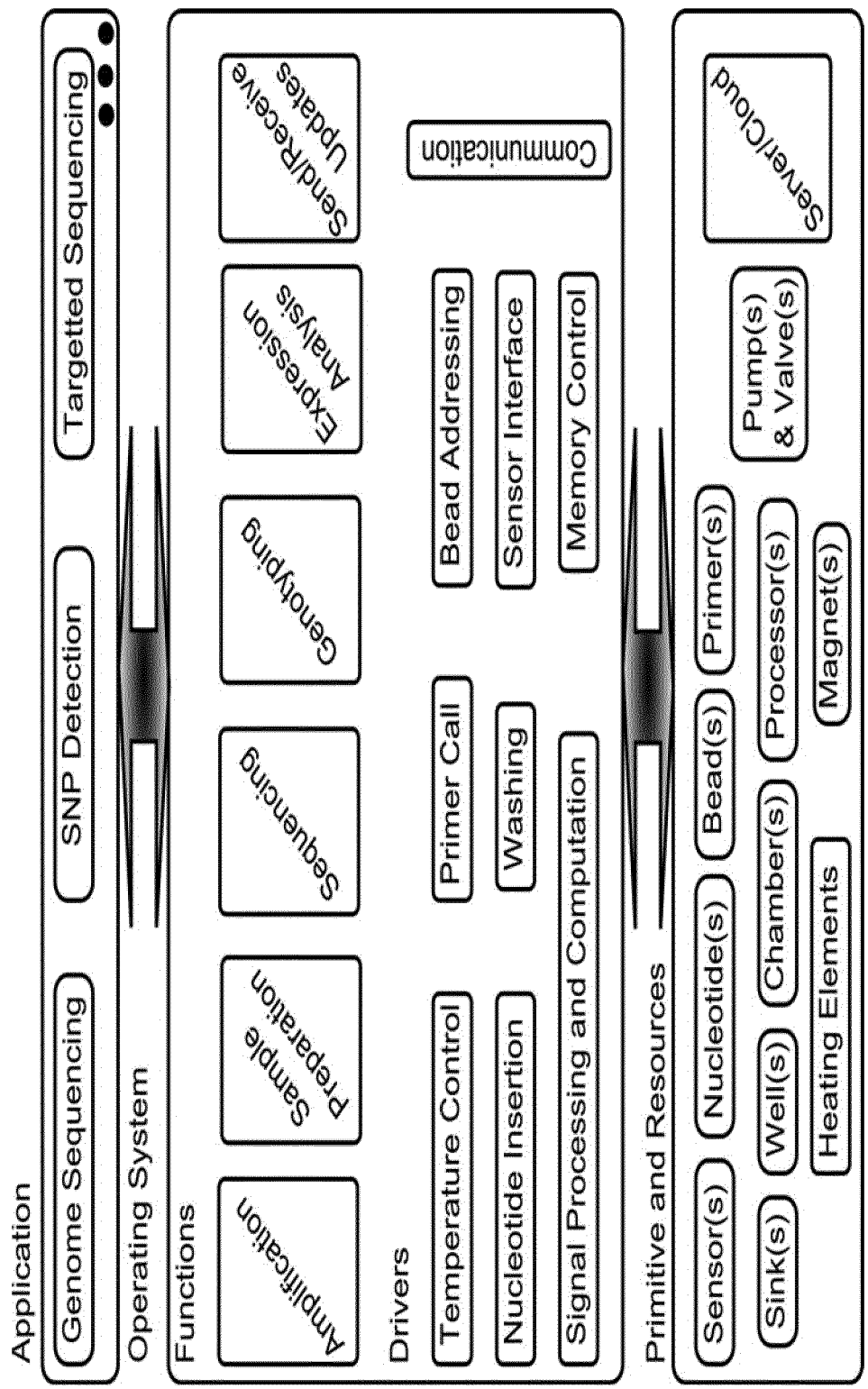
FIG. 7 illustrates schematically components of a "biological" operating system and an application layer for implementing biological workflows.

FIG. 7 illustrates schematically functional and structural features of a further exemplary instrument comprising an application layer, an operating system, and a set of primitives and resources. The Figure illustrates in particular that the operating system makes available to the application(s) a set of assay processes including amplification, sample preparation, etc.

Figure 8:
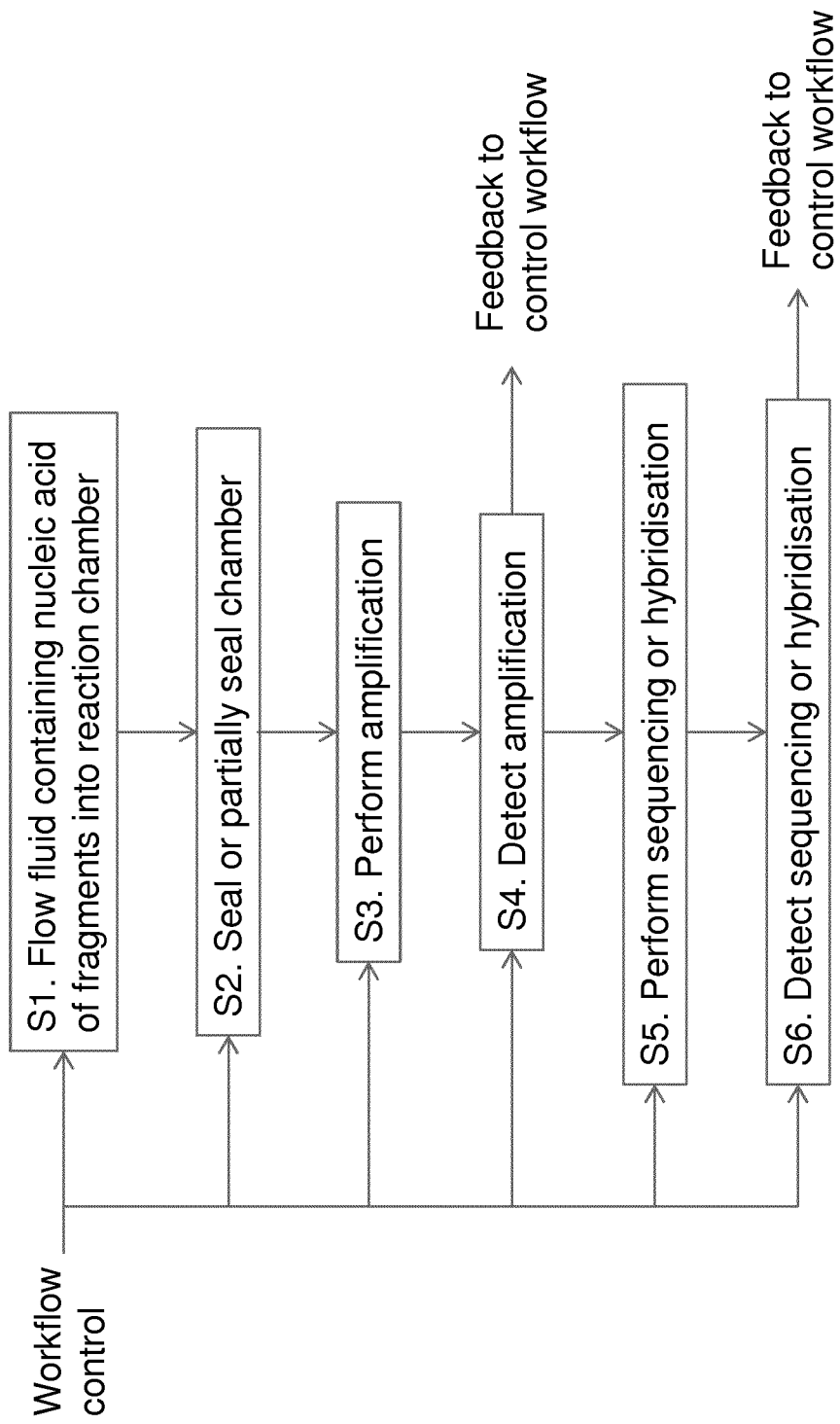
FIG. 8 is a flow diagram illustrating a process for analysing nucleic acid or fragments thereof.
Figure 9:
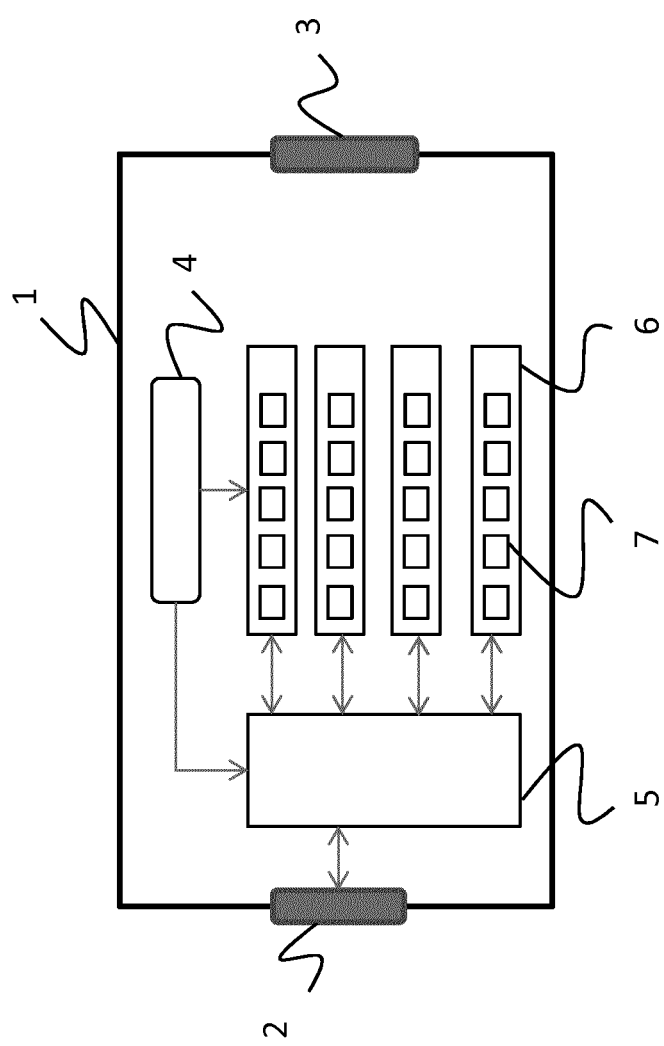
FIG. 9 illustrates schematically a cartridge suitable for implementing the method of FIG. 7.

FIG. 8 is a flow diagram illustrating a process for analysing nucleic acid or fragments thereof. A various points in the flow, detected outputs are provided to inform workflow decisions, and workflow control decisions are received. FIG. 9 illustrates schematically a cartridge 1 suitable for performing this analysis. The cartridge may be configured for use with an instrument that provides fluids to the cartridge via a fluid interface 2, and which exchanges data with the cartridge via a data interface 3. The cartridge comprises a controller 4 which controls a fluid transport system 5 fluidly coupled to the fluid interface 2. The controller also controls a set of reaction chambers 6, each of which comprises a set of sensors 7.

The invention claimed is:

1. Apparatus for analysing nucleic acid and comprising:
a cartridge having a multiplicity of reaction chambers with respective sensors, the sensors being configured or configurable to detect amplification, sequencing, and hybridisation in the reaction chambers;
a fluid transport system for controlling the flow of fluids, including fluids containing said nucleic acid or fragments of said nucleic acid, to the reaction chambers in order to facilitate a sequence of reactions including amplification, sequencing, and hybridisation of the nucleic acid and/or fragments thereof; and
a controller implemented on a computer, said computer coupled to said sensors and to said fluid transport system, said sensors configured for obtaining detection results including intermediate reaction sequence results, said controller configured to provide a control signal to said fluid transport system to dynamically direct the sequence of reactions for the analysis using the intermediate reaction sequence results, wherein the controller is programmed, based on data provided by the sensors, to determine an instance where there is no amplification, and, when the instance where there is no amplification is detected, the controller is programmed to provide a control signal to said fluid transport system to stop any further reactions taking place, and wherein the controller is further programmed to determine, based on data provided by the sensors, an instance where there is failure to detect hybridisation, and is further programmed to, when there is failure to detect hybridisation, provide a control signal to said fluid transport system to switch off downstream sequencing reactions.

2. Apparatus according to claim 1, wherein each of at least certain of the sensors are configurable to detect two or more of amplification, sequencing, and/or hybridisation in the reaction chambers.

3. Apparatus according to claim 1, wherein at least a part of said fluid transport system is provided on the cartridge, and the cartridge comprises fluid inlets and outlets for coupling the fluid transport system, or said part of said fluid transport system, to external fluid sources and fluid drains.

4. Apparatus according to claim 1, wherein said sensors are all of the same sensor type.

5. Apparatus according to claim 4, wherein said sensors are ChemFETs.

6. Apparatus according to claim 1, wherein at least some of said reaction chambers and associated sensors are configured, by means of amplification primers immobilised or contained within solutions in the reaction chambers, to implement a set of PCR (polymerase chain reaction) panels each performing PCR on a different targeted DNA sequence, the reaction chambers and sensors of a given panel of the panel set being configured to implement and detect the same reaction type.

7. Apparatus according to claim 6, wherein the controller is configured to operate the PCR panels of the panel set in parallel.

8. Apparatus according to claim 6, comprising a plurality of panel sets.

9. Apparatus according to claim 1, wherein said fluid transport system comprises one or more fluid flow control gates, under the control of said controller, for directing fluid to desired reaction chambers.

10. Apparatus according to claim 1, wherein each reaction chamber comprises a plurality of identical sensors.

11. Apparatus according to claim 1,
wherein the controller is configured for operating said reaction chambers and sensors; and
wherein, said controller is further configured to operate said reaction chambers and sensors in order to implement a workflow comprising two or more of a genetic amplification, sequencing, and hybridization, the workflow including one or more intermediate decision points dependent upon result data obtained from said sensors.

12. Apparatus according to claim 1, wherein said step of controlling said fluid transport system to dynamically direct the sequence of reactions for the analysis using the intermediate reaction sequence results includes providing a control signal to said fluid transport system to stop the reaction sequence directly after amplification or sequencing.

* * * * *